United States Patent [19]
Garth et al.

[11] Patent Number: 5,878,748
[45] Date of Patent: Mar. 9, 1999

[54] APPARATUS FOR PROVIDING FOOT AND LEG SUPPORT FOR AN IMMOBILIZED PATIENT

[75] Inventors: Geoffrey Campbell Garth, Long Beach; John Curtis Hamilton, Rancho Santa Margarita, both of Calif.

[73] Assignee: International Healthcare Devices, Long Beach, Calif.

[21] Appl. No.: 941,377

[22] Filed: Sep. 30, 1997

[51] Int. Cl.[6] .................................................. A61B 19/00
[52] U.S. Cl. ........................................ 128/869; 128/882
[58] Field of Search ................................. 128/846, 869, 128/878, 879, 882; 602/15, 28, 27, 29, 23; 5/624, 648, 650, 651

[56] References Cited

U.S. PATENT DOCUMENTS

| | | | |
|---|---|---|---|
| 3,624,745 | 11/1971 | Bowers | 602/15 |
| 4,383,526 | 5/1983 | Robins | 602/15 |
| 5,441,015 | 8/1995 | Farley | 602/28 |
| 5,603,692 | 2/1997 | Maxwell | 128/882 |

*Primary Examiner*—Michael A. Brown
*Attorney, Agent, or Firm*—Kenyon & Kenyon

[57] ABSTRACT

An apparatus provides foot and leg support for an immobilized patient. The apparatus is designed to adapt to the lower leg of the patient while providing sufficient support while avoiding cell death that can lead to skin damage. Furthermore, the structure is provided to prevent foot drop while enhancing the storability of the device when not in use.

13 Claims, 4 Drawing Sheets

APPARATUS FOR PROVIDING FOOT AND LEG SUPPORT FOR AN IMMOBILIZED PATIENT

BACKGROUND OF THE INVENTION

The present invention is directed to an apparatus for providing foot and leg support for an immobilized patient. More particularly, the present invention provides a device that provides appropriate support to a foot and a leg so as to prevent foot drop while avoiding skin damage.

It is well known in the medical community that prolonged periods of immobility where a patient is forced to remain in a single position, for instance in a bed ridden prone position, can create significant skin problems, commonly referred to as bed sores. These skin problems arise from the fact that when too much pressure is brought to bear on the skin, capillary refill cannot occur in the cardiovascular system. As a consequence, cell death begins in the skin.

A common way to avoid this problem is to somehow provide a change of position for the patient so that the same portions of the body are not bearing the weight on the supporting surface during the period of the patient's immobility. However, this can be a taxing process for certain patients. It is therefore a goal to provide as much support for the patient's body as possible while avoiding the creation of these bed sores and without further complicating patient treatment.

Additional problems arise when one considers the impact of immobility upon a patient's leg and foot. In particular, the heel of a patient's foot, upon which the pressure of the foot would typically rest in an immobile patient laying on his or her back, does not have much flesh between the skin and bone. Therefore, this area is more readily susceptible to cell death and ultimately skin damage. Furthermore, the large muscle of the lower leg and foot contract to pull the foot downward, away from the leg so as to create a condition commonly referred to as foot drop. In foot drop, the foot is pulled away from a position of function, that is the normal angular position of the foot with respect to the leg, generally around 90° or so.

It has been known to provide supporting structures for a patient's leg and foot. For instance, U.S. Pat. No. 5,603,692 to Maxwell discloses a drop foot splint. The splint includes an L-shaped supporting mechanism which maintains the foot at approximately a right angle with respect to the leg. However, a splint such as that shown in Maxwell does have a number of drawbacks. For instance, the splint is more difficult to store since it is in a fixed L-shape. Furthermore, as shown in FIG. 2, the support for the patient's foot is provided along the heel and the calf alone and is not really distributed along the lower leg portion so as to more evenly distribute the leg's weight. This can lead to a potential problem with skin death, particularly at the heel.

It would be beneficial for patients and medical practitioners to have available a foot and leg support that prevents foot drop and skin damage while still providing an easily stored structure.

SUMMARY OF THE INVENTION

The present invention provides a foot and leg support which supports the leg of an immobilized patient while at the same time avoiding skin death and preventing foot drop. In accordance with an embodiment of the present invention the apparatus includes a first leg support component that includes a flexible structure that can be adaptable to a lower leg of a patient to which it is applied and a foot support component that is connected to an end of the first leg support component so as to prevent foot drop when applied to a patient's leg.

The apparatus of the present invention can be constructed out of cardboard. It is further possible that both a leg support component and the foot support component can be made together out of a continuous piece of cardboard. In the latter case foldability can be provided by appropriately scoring the cardboard to create folds that enable the leg support component and the foot support component to come together in a stored position and to come apart and form an L-shape when it is to be applied to a patient's leg. The top surface of the leg supporting member can also include cardboard appropriately scored as to better adapt to the patient's lower leg. Furthermore, the structure can include areas of differing flexibility so as to provide a more flexible portion in the area of the lower leg adjacent the heel of the patient while providing a firmer structure in the area adjacent to the patient's calf.

As a consequence of the design, the present invention provides foot and leg support for a patient while avoiding skin death and foot drop.

DETAILED DESCRIPTION

Figure 1:
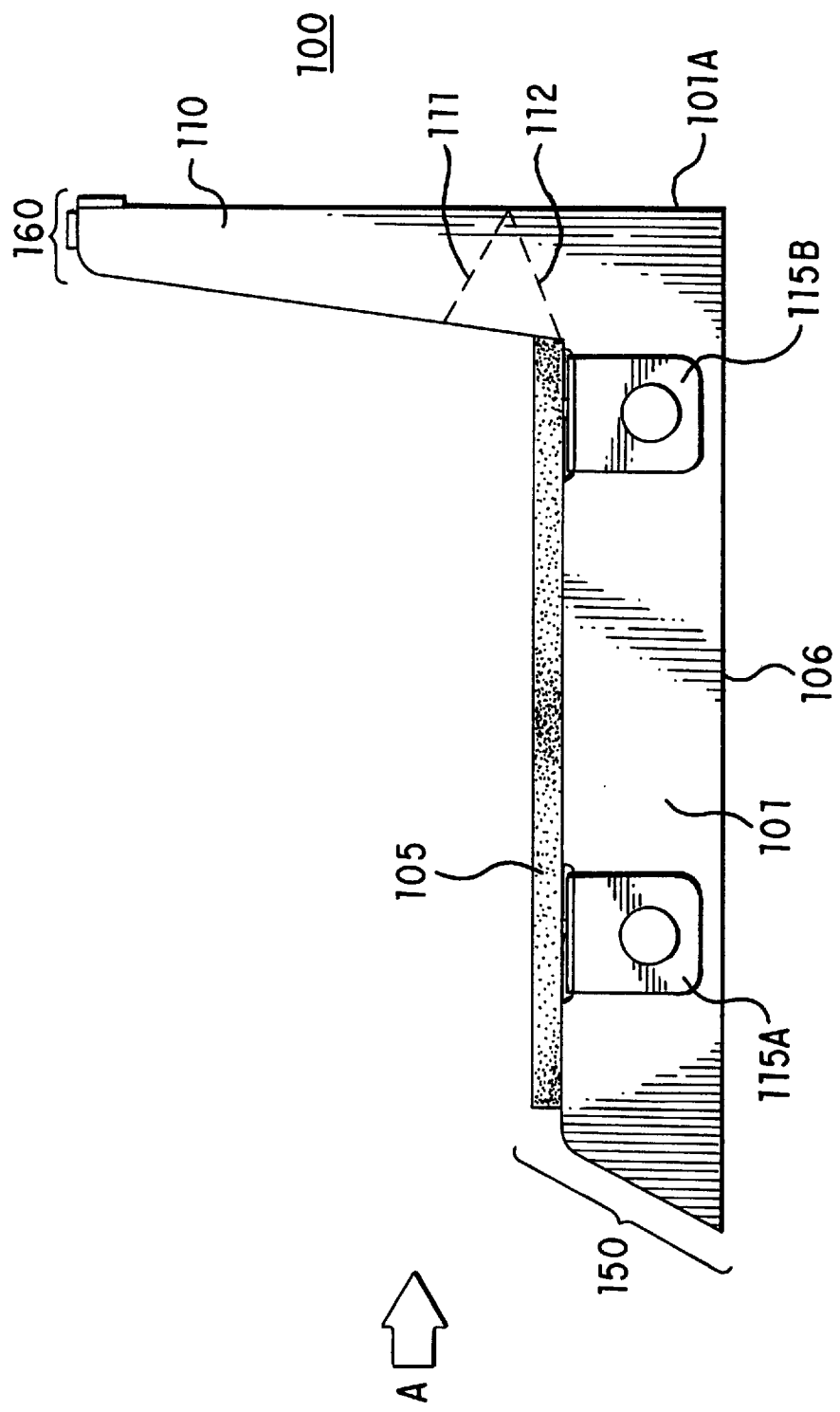
FIG. 1 illustrates a first side view of an embodiment of the present invention.

An apparatus of the present invention will now be described with reference to the drawing figures. In those figures like elements bear identical reference numerals.

A first side view of an embodiment of the present invention is illustrated in FIG. 1. A leg and foot supporting apparatus 100 has a leg supporting structure 150 and a foot supporting structure 160. When configured for application to a patient the foot supporting structure and leg supporting structure form approximately a right angle. This orientation operates to maintain the patient's foot in a position of function, that is it prevents foot drop.

The leg supporting structure includes a bottom surface 106 which is adapted to come into contact with a structure on which the immobilized patient's leg is to be placed. That could be a flat surface such as a bed. Alternatively, the leg supporting structure could be placed in some sort of sling-like surface or any other surface that medical practitioners feel is appropriate for keeping the leg in a particular orientation. The leg supporting structure also includes a side wall 101. A top surface of the leg supporting structure can include a pad 105 which can be constituted by some flexible material such as foam. An example of the type of foam which might e utilized is an ester foam. Other types of pads are useable. The pad may have either a flat configuration or some sort of waffle like configuration depending on the practitioner's choice.

Figure 2:
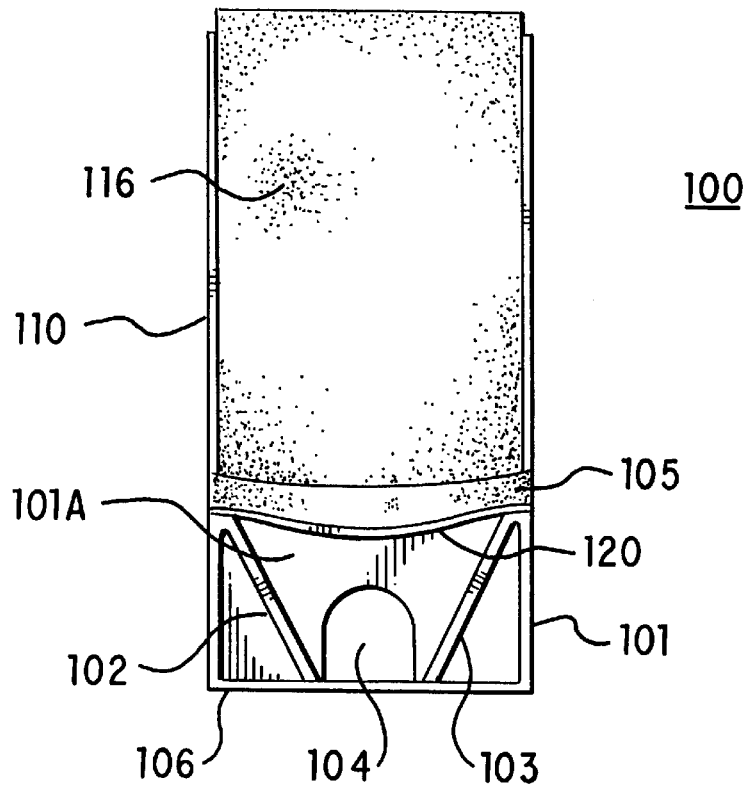
FIG. 2 illustrates a first frontal view of an embodiment of the present invention.
Figure 3:
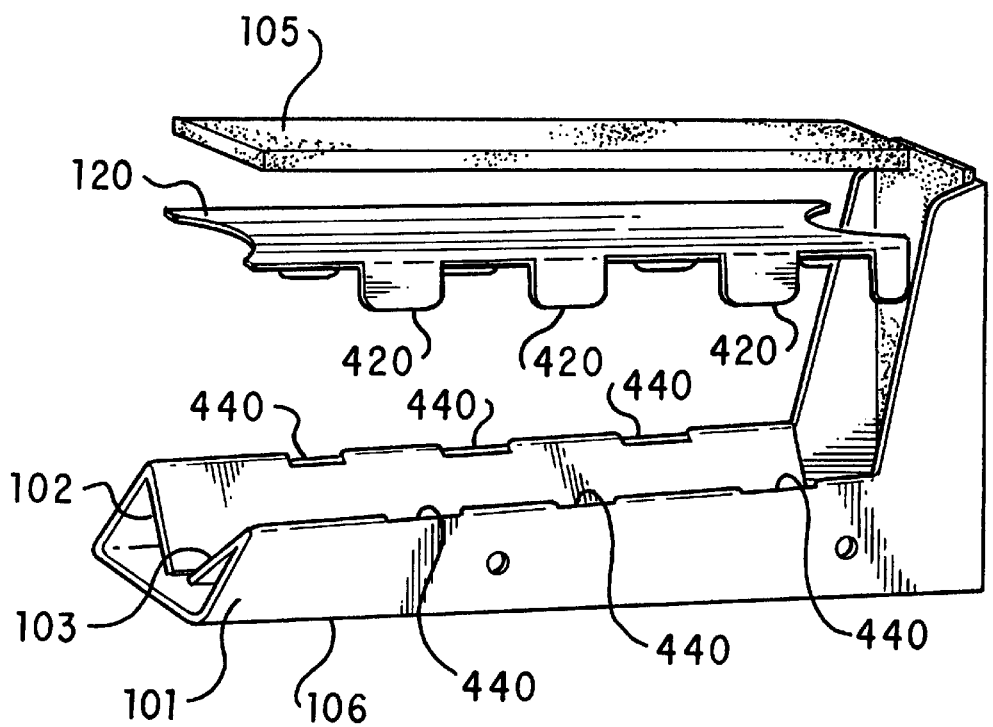
FIG. 3 illustrates an exploded side view of the embodiment of the present invention of FIGS. 1 and 2.

The structure of the leg support 150 can be better understood with reference to FIG. 2 which shows a view of the apparatus from the perspective of "A" looking along the arrows shown in FIG. 1. The leg supporting structure can have its bottom surface 106 and side surface 101 formed of the same material. In one embodiment of the present invention this is a sheet of material such as cardboard. Other examples of materials which could be used for this purpose include corrugated plastic sheet, polyethylene sheet material of an appropriate thickness. The continuous sheet of material can be folded over to form internal angular walls 102 and 103. The walls can be fastened to the bottom surface in many different ways. In one variation the wall ends have multiple tabs that are insertable into slots in the bottom surface. The elements can be further affixed using some sort of adhesive. The result is the creation of a concave space 101A that runs the length of the leg supporting structure 150. At the top of the leg supporting structure is a lower leg supporting member forming a top surface and includes a supporting surface 120 and pad 105. The supporting surface 120 can also be made of cardboard. The lower leg supporting member is designed so as to be supported above the concave space only along the edges of the member. This allows the member to adapt to the patient in much the same way a hammock, supported at its edges, adapts to the weight applied thereto. Furthermore, as shown in FIGS. 3 and 4 this supporting surface 120 can be constructed so that it not only is connected at its edges but is also detachable from the remainder of the leg supporting structure.

The illustrated structure provides both rigidity in terms of its lower portions and flexibility in terms of its upper portions. More specifically, the hard bottom surface 106, hard side walls and hard diagonal walls 102 and 103 create a rigid structure which can be placed upon a supporting surface upon which the leg and leg support are ultimately laid to rest. By contrast, the upper surface comprised of the supporting surface 120 can be made to be flexible so as to collapse or bend into the concave space 101A as it adapts to the pressure applied by a leg resting atop pad 105. This flexibility can be accomplished, for instance, by scoring a top of supporting surface 120 along multiple areas so that as pressure in the form of the patient's leg is applied to the top of the surface, that surface will bend or fold along multiple lines and thereby provide adaptable support for the patient's leg. An example of such scoring is illustrated in FIG. 4. Specifically, the dashed lines 401 represent areas of scoring. The leg supporting member could be provided with or without pad 105. The pad however may provide additional comfort to the patient's leg and aid in the efforts to prevent skin damage. In such a case the pad 105 could be fixed to the upper portion or supporting surface 120 by any one of many fastening techniques such as by adhesives, rivets, velcro attachments, etc. However, the construct of the upper portion 120 could be configured so as to provide sufficient flexibility to avoid skin damage without need of pad 105.

Figure 4:
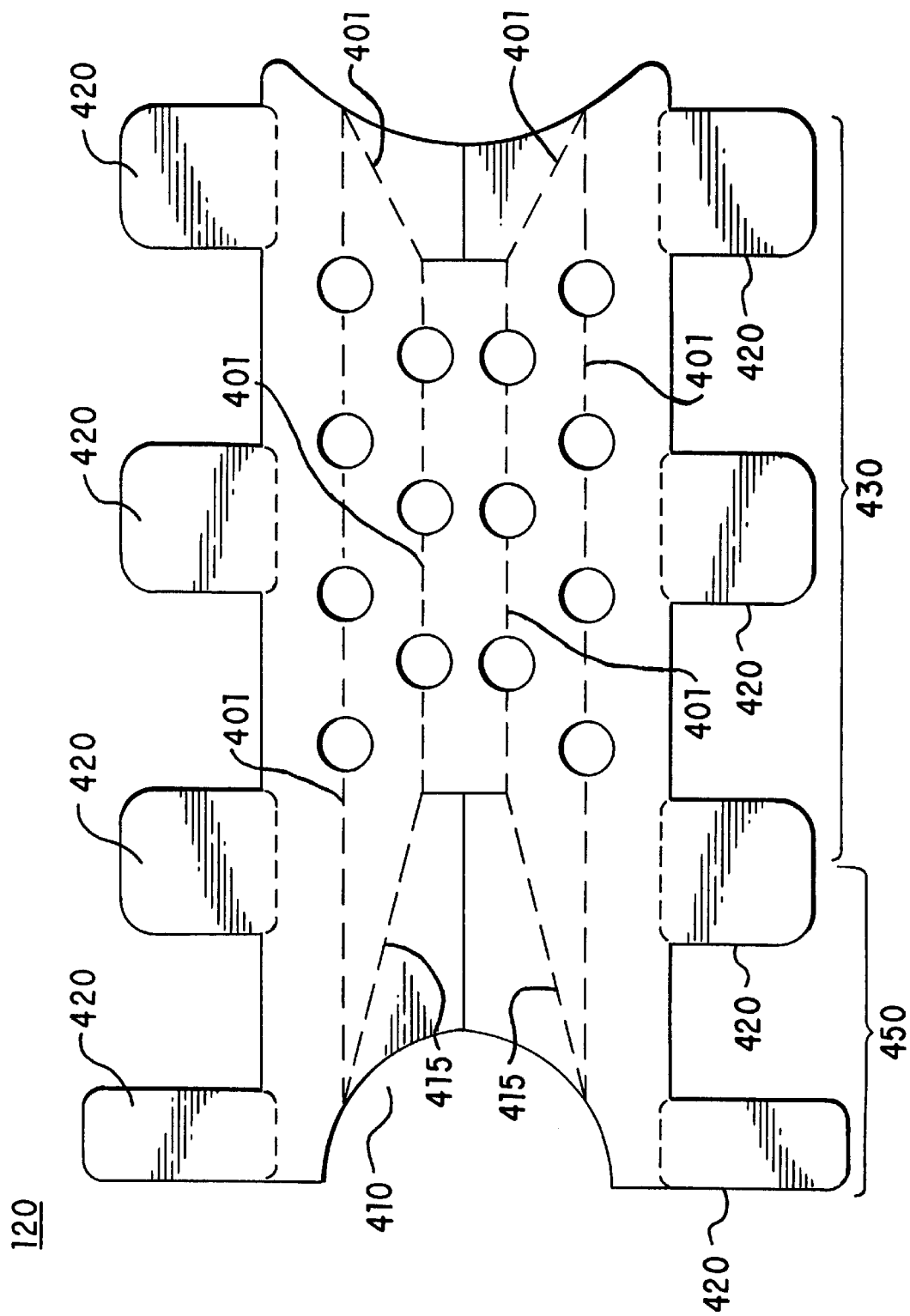
FIG. 4 illustrates a top surface of a supporting component of the embodiment shown in FIGS. 1 to 3.

A further feature of element 120 is also illustrated in greater detail in FIG. 4 where it is shown that the flexibility of the structure varies over the length of the structure. More particularly, in the region of the structure that would be adjacent the calf portion of the patient's leg, 430, the structure has a first level of flexibility largely defined in this embodiment by the scoring of the cardboard. However, the element 120 has additional flexibility in the region adjacent to the patient's heel (450) as shown by the opening 410 created in that portion and the folds 415 built into that portion whereby the leg and heel can rest on the top of surface 120 in a hammock-like fashion. The heel then extends into the aperture created by the opening in the end of the supporting surface 120. This drawing figure also shows that the portion 120 can have a plurality of tabs 420, also shown in the exploded view of FIG. 3, which allows the portion 120 to be detachable from the remainder of the leg supporting structure. The tabs 420 are insertable into slots 440. This is meant to show just one example of how the component can be coupled to the remainder of the structure.

Returning to FIG. 2, the view shown also illustrates an opening or aperture 104 that is provided in a back wall portion of the lower leg support, wall portion 101A. Opening 104 provides for a flow of air through the apparatus that aids in reducing the likelihood of perspiration as perspiration can increase the likelihood of skin damage when pressure is applied to an area subjected to perspiration over an extended period of time.

Figure 5:
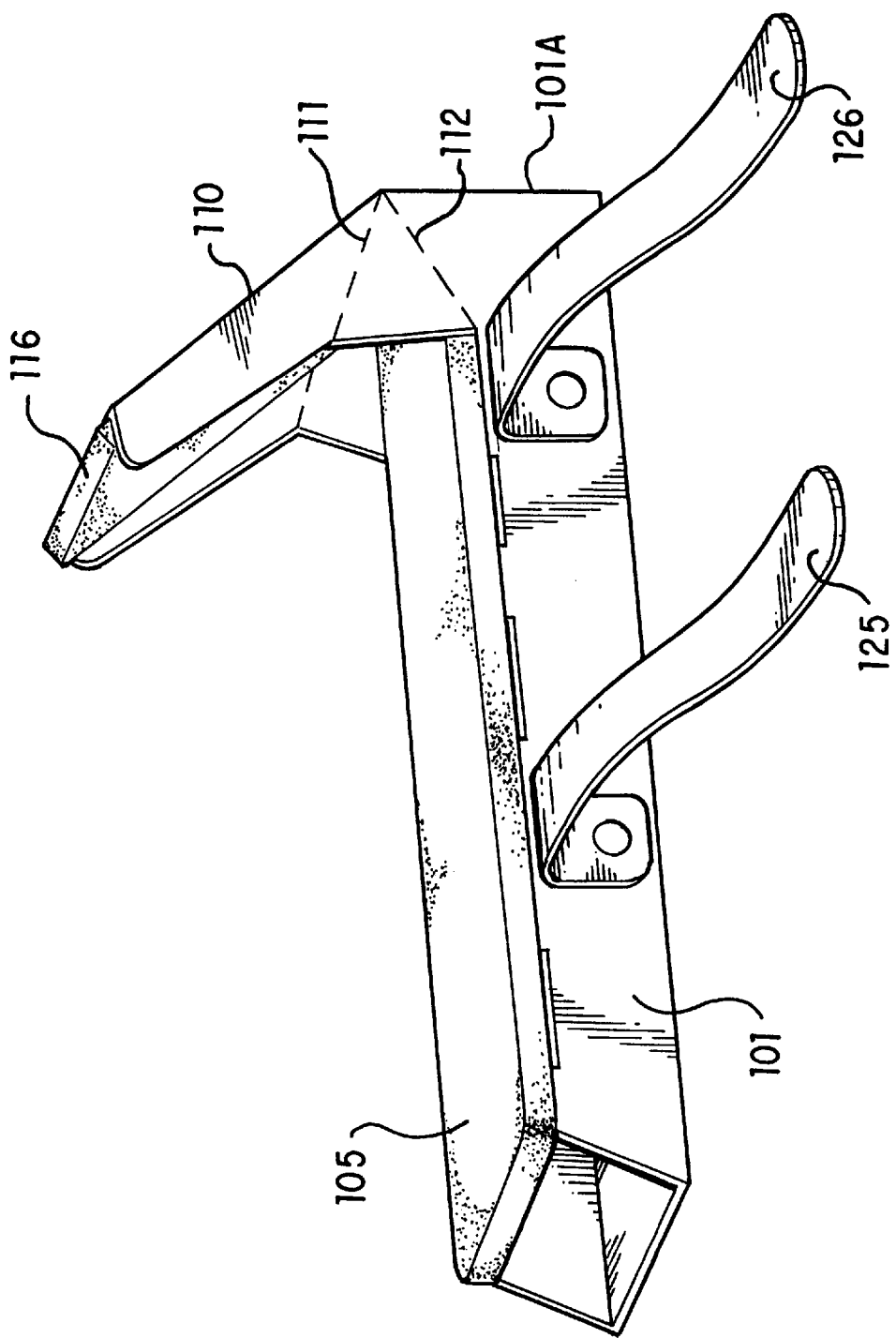
FIG. 5 illustrates a side view of a folded structure in accordance with an embodiment of the present invention.

The foot support portion 160 includes a foot support 110 which is continuous with the wall portions of the leg support 101. The material is processed in areas 111 and 112 as shown in FIG. 5 so as to permit the foot support portion to be foldable with respect to the leg support portion. The result of this foldability is better illustrated in FIG. 5 which provides a side view of an embodiment of the present invention. Using these folds 111 and 112, and similar folds on the opposite side of the foot support (not shown) the foot support portion can be brought to extend over and above the leg support portion and can essentially be stored flat on top of the leg support portion. This improves the storability of the device as it can be converted from an L-shape to a flat configuration and then back again for use. In this configuration since the leg support portion is constituted by the same structure as the leg support portion it could be expected that if the leg support portion is composed of cardboard then the foot support portion would also be composed of cardboard. However, in alternative embodiments different materials might be used for the foot support and leg support. Furthermore, rather than providing a continuous connection of the leg and foot supports, the two supporting members could be constituted by two distinct pieces that are joined together by fasteners to either provide foldability or a flexible connection which allows the same adaptation from a storage position to a use position.

The foot supporting portion can further be modified to include a pad 116 to provide further comfort to the wearer. This pad could be constituted by the same material as pad 105 or could be selected from another group of materials. Furthermore, to provide additional comfort, the pad 116 can be made to extend past an edge of the foot support 110 that is formed by the lip 122.

It is beneficial to secure such leg/foot support apparatus to the immobilized patient. One way to do so would be to provide straps such as those shown as 125 and 126 in FIG. 5 that can cooperate with the Velcro tabs on the opposite side surface (not shown). These straps and connectors allow the apparatus to be fastened around a patient's leg so as to fix the application of the apparatus to the patient. Of course, other strap configurations could be utilized.

The arrangement of the leg supporting portion, especially the flexibility provided to supporting surface 120 and its relationship to the more rigid member constructed of walls 101, bottom surface 106 and diagonal surfaces 102 and 103 presents a structure which prevents skin damage to the underside of the leg while the supporting mechanism holds the leg. It does so by properly distributing the weight of the leg along the entirety of the surface so as to avoid pressure points that exceed that value of pressure at which skin death occurs. Furthermore, the foot support arrangement provides a flexible attachment of an element which prevents foot drop when extended and applied to the patient but also permits easy storage of the device because of the foot support's flexibility with reference to its positioning relative to the leg supporting member. In particular, the relative movement could include the foldability of the foot support with regard to the leg support member.

In accordance with the embodiment of the present invention, the apparatus provides appropriate protection against foot drop and avoids skin damage where a patient's leg needs to be immobilized for a significant portion of time.

What is claimed is:

1. An apparatus for providing foot and leg support for an immobilized patient, the apparatus comprising:
    a leg support component that includes;
        a bottom surface,
        a concave top surface, and
        a lower leg supporting member, coupled to said concave top surface, said lower leg supporting member having a flexible structure adaptable to a lower leg of a patient to which it is applied, said member including;
            a first region adapted to support a patient's calf, and
            a second region, of higher flexibility than said first region adapted to support a patient's heel; and
    a foot support component, connected to an end of said leg support component, wherein when the leg support component and foot support component are applied to a patient, the patient's foot is maintained in the position of function.

2. The apparatus of claim 1 wherein said leg support component and said foot support component comprise cardboard.

3. The apparatus of claim 2 wherein said lower leg supporting member includes a cardboard structure.

4. The apparatus of claim 3 wherein said cardboard structure of said lower leg supporting member includes a first processed surface that facilitates bending of the structure along a plurality of lines.

5. The apparatus of claim 1 wherein said foot support component is foldably connected to an end of said leg support component.

6. The apparatus of claim 5 wherein said foot support component is integral with said leg support component.

7. The apparatus of claim 5 wherein said foot support component and said leg support component both comprise cardboard.

8. The apparatus of claim 1 wherein said foot support component is fixedly attached to the leg support component.

9. An apparatus for providing foot and leg support for an immobilized patient, the apparatus comprising:
    a leg support component that includes;
        a bottom surface;
        a concave top surface; and
        a lower leg supporting member, coupled to said concave top surface, said lower leg supporting member having a flexible structure adaptable to a lower leg of a patient to which it is applied, wherein said lower leg supporting member is detachably coupled to said concave top surface to allow attachment and subsequent removal; and
    a foot support component, connected to an end of said leg support component, wherein when the leg support component and foot support component are applied to a patient, the patient's foot is maintained in the position of function.

10. An apparatus for preventing foot drop for an immobilized patient whose leg is to be supported on supporting surface, the apparatus comprising:
    a hammock portion having a bottom surface that can rest on the supporting surface and a top surface upon which the patient's leg can be positioned wherein said hammock portion includes,
        a bottom support member having said bottom surface and a top concave surface wherein said bottom surface and said top concave surface are formed of a stiff material, and
        a top support member coupled to said top concave surface and providing said top surface, the top support member including a flexible material adaptable to a leg surface with which it comes in contact wherein said top support member is detachably coupled to said top concave surface to allow attachment and subsequent removal; and
    a foot support, movable with respect to said hammock portion between a first position and a second position, wherein in a first position the foot support extends over the top supporting surface of the hammock portion and in a second position is at an angle of about 90° with respect to said hammock portion.

11. The apparatus of claim 10 wherein said top support member is foldable along a plurality of lines extending from a position adjacent a patient's calf toward said foot support as positioned in its second position.

12. The apparatus of claim 10 wherein said hammock portion and said foot support comprise cardboard.

13. An antidecubitus, leg and foot supporting apparatus, comprising:
    a leg supporting member having a flexible top surface resting above a bottom surface with a hollow channel in between, the top surface having regions of varying flexibility to allow for adaptation for a leg brought into contact with said top surface; and
    a foot supporting member flexibly coupled to said leg supporting member and when applied to a patient extends at approximately a right angle to said leg supporting member, said foot supporting member providing resistance to foot drop.

* * * * *

UNITED STATES PATENT AND TRADEMARK OFFICE
CERTIFICATE OF CORRECTION

PATENT NO. : 5,878,748
DATED : Mar. 9, 1999
INVENTOR(S) : Geoffrey C. Garth et al It is certified that error appears in the above-indentified patent and that said Letters Patent is hereby corrected as shown below:

| Column | Line | |
|---|---|---|
| 2 | 62 | Change "e utilized" to --be utilized--. |
| 6 | 22 | Change "materal" to --material--. |

Signed and Sealed this

Fifth Day of October, 1999

Attest:

Q. TODD DICKINSON

Attesting Officer     Acting Commissioner of Patents and Trademarks